United States Patent
Soto León et al.

(10) Patent No.: US 11,844,791 B2
(45) Date of Patent: Dec. 19, 2023

(54) USE OF ANTAGONISTS AND/OR INVERSE AGONISTS OF CB1 RECEPTORS FOR PREPARING MEDICAMENTS FOR TREATING FATIGUE POST-VIRAL FATIGUE SYNDROME

(71) Applicant: FUNDACION HOSPITAL NACIONAL DE PARAPÉJICOS, Toledo (ES)

(72) Inventors: Vanesa Soto León, Toledo (ES); Manuel Nieto Díaz, Toledo (ES); Antonio Oliviero, Toledo (ES)

(73) Assignee: FUNDACION HOSPITAL NACIONAL DE PARAPEJICOS, Toledo (ES)

( * ) Notice: Subject to any disclaimer, the term of this patent is extended or adjusted under 35 U.S.C. 154(b) by 0 days.

(21) Appl. No.: 17/526,405

(22) Filed: Nov. 15, 2021

(65) Prior Publication Data
US 2022/0152010 A1   May 19, 2022

(30) Foreign Application Priority Data
Nov. 18, 2020 (EP) ...................... 20382995

(51) Int. Cl.
*A61K 31/454* (2006.01)
*A61P 25/26* (2006.01)

(52) U.S. Cl.
CPC ............ *A61K 31/454* (2013.01); *A61P 25/26* (2018.01)

(58) Field of Classification Search
CPC ............................ A61K 31/454; A61P 25/26
See application file for complete search history.

(56) References Cited

U.S. PATENT DOCUMENTS 9,238,027 B2   1/2016   Oliviero et al.
9,592,237 B2   3/2017   Oliviero et al.

FOREIGN PATENT DOCUMENTS

| EP | 0656354 A1 | 6/1995 |
| EP | 2397137 A1 | 12/2011 |
| WO | 2008074816 A1 | 6/2008 |

OTHER PUBLICATIONS

Munblit et al (BMC Medicine, 2022; 20:50 pp. 1-13) (Year: 2022).*
Yong et al (Infections Diseases, 2021; 53(10):737-754) (Year: 2021).*
Joaquim P. Brasil-Neto, "Postexercise depression of motor evoked potentials: a measure of central nervous system fatigue", Journal, 1993, 181-184, vol. 93, Experimental Brain Research.
A. Oliviero, "CB1 receptor antagonism/inverse agonism increases motor system excitability in humans", Journal, 2012, 27-35, vol. 22, European Neuropsychopharmacology.

* cited by examiner

*Primary Examiner* — Rayna Rodriguez
(74) *Attorney, Agent, or Firm* — Hayes Soloway PC

(57) ABSTRACT

The invention relates to the use of an antagonist and/or inverse agonist of CB1 receptors, in particular Rimonabant, in the treatment of post-viral fatigue syndrome, and more particularly, for the preparation of medicaments useful for treating fatigue after COVID-19. A method of treating post-viral fatigue syndrome in COVID-19 patients comprising administering a therapeutically effective amount of a pharmaceutical composition comprising an antagonist and/or inverse agonist of CB1 receptors.

6 Claims, 2 Drawing Sheets

USE OF ANTAGONISTS AND/OR INVERSE AGONISTS OF CB1 RECEPTORS FOR PREPARING MEDICAMENTS FOR TREATING FATIGUE POST-VIRAL FATIGUE SYNDROME

CROSS-REFERENCE TO RELATED APPLICATIONS AND PRIORITY

This patent application claims priority from European Patent Application No. 20382995.7 filed Nov. 18, 2020. This patent application is herein incorporated by reference in its entirety.

TECHNICAL FIELD

The invention relates to the use of an antagonist and/or inverse agonist of CB1 receptors, in particular Rimonabant, in the treatment of post-viral fatigue syndrome, and more particularly, for the preparation of medicaments useful for treating fatigue after COVID-19.

BACKGROUND ART

The endogenous cannabinoid system is formed by endogenous ligands, their synthesizing enzymes and degrading enzymes and two different specific receptors cloned to date: cannabinoid receptor 1 (CB1), and cannabinoid receptor 2 (CB2). Cannabinoid receptor type 1 (CB1) receptor agonists may reduce spasticity and pain in a number of neurological, rheumatic, traumatic diseases and in cancer. CB1 receptor agonism lead to an induction of sleep.

Rimonabant is the international non-proprietary name for N-(piperidino-1-yl)-5-(4-chlorophenyl)-1-(2,4-dichlorophenyl)-4-methylpyrazole-3-carboxamide described in EP656354 as an antagonist/inverse agonist of CB1 receptor. Its capacity to increase the excitability of motor neurons have been described and the use of these antagonists/inverse agonists of CB1 as active ingredients in the treatment of a series of conditions has been proposed (U.S. Pat. Nos. 9,238,027B2; 9,592,237B2).

On the other hand, fatigue can be defined as the temporary loss of power to respond characterized by lack of energy, muscle weakness, slowed reactions, drowsiness and difficulties in concentration. Post-viral fatigue syndrome can result from biological, behavioural and environmental factors. Its main symptoms comprise muscle fatigability and pain, but also central nervous system abnormalities, such as sleep disturbances, depression, anxiety, and emotional lability. Fatigue is a multifaceted, challenging phenomenon that involves peripheral (muscular), central (e.g. cortico-spinal) and cognitive components.

Muscle (peripheral) fatigue is a reduction in maximal voluntary muscle force resulting from exercise. Peripheral fatigue is caused by the progressive muscular failure of force-generating capacity and the impulse conduction failure at the neuromuscular junction. On the contrary, the term "central fatigue" refers to the progressive loss in the capability of the central nervous system to maximally activate muscles. Central fatigue is caused by a decrease of excitability of corticospinal neurons within the primary motor cortex or due to failure to be activated by structures upstream the primary motor cortex, such as the premotor area and the basal ganglia, leading to a reduction in the signalling from the motor cortex to the spinal motorneurons.

Finally, fatigue may also result from sustained mental work, which leads to a decline in cognitive function known as cognitive fatigue.

Additionally, people may have increased perception of effort that worsens their performance after prolonged periods of cognitive and/or physical activity. The feeling—known as "mental fatigue"—differs from central fatigue because it does not affect the capacity of the central nervous system to recruit muscles.

SUMMARY OF THE INVENTION

The present invention discloses a novel use of an antagonist and/or inverse agonist of CB1 receptors for the preparation of medicaments useful for treating fatigue after COVID-19 and more in general post-viral fatigue syndrome. Preferably, said antagonist/inverse agonist is Rimonabant.

In the present invention is has been demonstrated that multiple COVID-19 patients show symptoms long-lasting after recovery from the acute phase of the infection. Among these symptoms, fatigue is prevalent in 53.1% of the patients.

Therefore, a first aspect of the present invention related to an antagonist and/or inverse agonist of CB1 receptors for use in the treatment of post-viral fatigue syndrome in COVID-19 patients.

In a preferred embodiment, the antagonist and/or inverse agonist of CB1 receptors is rimonabant.

Furthermore, in the present invention it has been demonstrated that Rimonabant increases excitability of the human motor system. Motor system excitability is reduced and related to fatigue after SARS-CoV-2 infection and COVID-19, and more in general post-viral fatigue syndrome.

Therefore, a further embodiment of the present invention provides an antagonist and/or inverse agonist of CB1 receptors for use in the preparation of a medicament for increasing the excitability of motor system and wherein said medicament further increases the activity of ascending arousal system to reduce fatigue, and more in general post-viral fatigue syndrome, in COVID-19 patients.

Another embodiment of the invention refers to a pharmaceutical composition comprising an antagonist and/or inverse agonist of CB1 receptors for use in the treatment of post-viral fatigue syndrome in COVID-19 patients.

In a preferred embodiment, the antagonist and/or inverse agonist of CB1 receptors is Rimonabant.

Unless otherwise expressly the pharmaceutical composition is administered in a form of administration selected from the group consisting of oral, sublingual, subcutaneous, intramuscular, intravenous, topical, local, intratracheal, intranasal, transdermal or rectal.

In another preferred embodiment, the pharmaceutical compositions according to the present invention contain an effective dose of at least one agonist and/or inverse agonist of CB1 receptors, and at least one pharmaceutically acceptable excipient. The above said excipients are chosen according to the pharmaceutical dosage form and the method of administration desired, from the usual excipients which are known to persons skilled in the art.

In another preferred embodiment, the effective daily dose of the antagonist and/or inverse agonist of CB1 receptors ranges from 1 mg to 50 mg per dose.

In another preferred embodiment, the pharmaceutical compositions of the present invention may be administered in a unit form for administration, mixed with conventional pharmaceutical excipients, to animals and to human beings for increasing the excitability of the motor neurons at cortical, brainstem and spinal level and/or to increase the activity of ascending arousal system in COVID-19 patients.

In the pharmaceutical compositions of the present invention, the active ingredient may be administered in a unit form for administration, mixed with conventional pharmaceutical excipients, to animals and to human beings to treat and/or to reduce symptoms of those diseases characterized by fatiguing dysfunction caused by COVID-19.

In the pharmaceutical compositions of the present invention, the active ingredient may be administered in a unit form for administration, mixed with conventional pharmaceutical excipients, to animals and to human beings to treat those diseases characterized by excessive fatigue like fatigue after covid-19 and more in general post-viral fatigue syndrome.

The appropriate unit forms for administration comprise the forms for oral administration such as tablets, soft or hard gelatine capsules, powders, granules and oral solutions or suspensions, the forms for sublingual, buccal, intratracheal, intraocular or intranasal administration, or for administration by inhalation, the forms for topical, transdermal, subcutaneous, intramuscular or intravenous administration, the forms for rectal administration and implants.

The term "COVID-19 patients" as used herein refers to COVID-19 patients which show symptoms long-lasting after recovery from the acute phase of the infection.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples and drawings are provided by way of illustration and are not intended to be limiting of the present invention.

DESCRIPTION OF THE DRAWINGS

FIG. 1A: General fatigue was measured using the fatigue severity score and it was higher in the COVID-19 group (median±S.D. 38±10.8) in comparison with healthy controls (median±S.D. 9.5±0.5; *Mann-Withney Test p<0.001). FIG. 1B: Fatigue perception after a motor effort (1 min isometric task) was measured using the Borg Scale and it was higher in the COVID-19 group (median±S.D. 75±15.6) in comparison with healthy controls (median±S.D. 54.6±9.7; Unpaired T test, p<0.001). FIG. 1C: Motor system excitability (MEP amplitude) was lower in the COVID-19 group (mean±S.D. 0.8±0.5 mV) in comparison with healthy controls (mean±S.D. 1.9±1.2 mV, Unpaired T test, p=0.001).

EXAMPLES

Figure 1A:
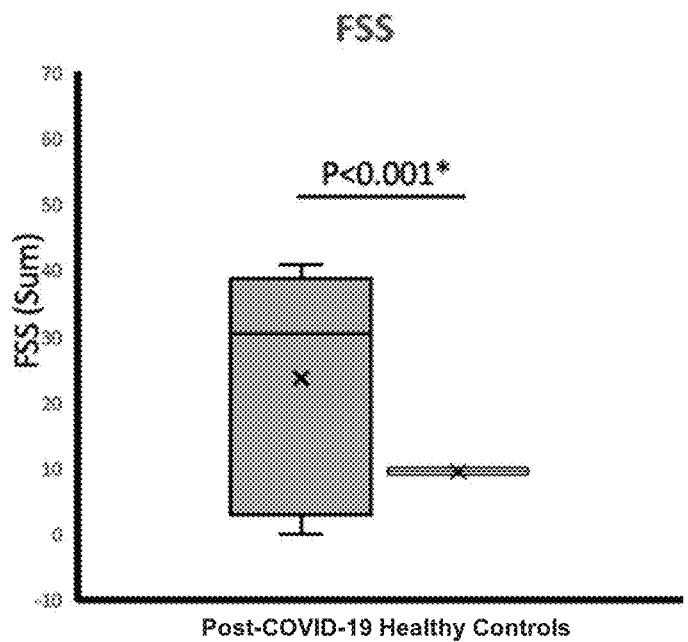
FIGS. 1A-1C. General fatigue (FSS), fatigue perception (Borg Scale) and motor system excitability (MEP amplitudes) in a post COVID-19 patient compared to healthy age-matched individuals.
Figure 1B:
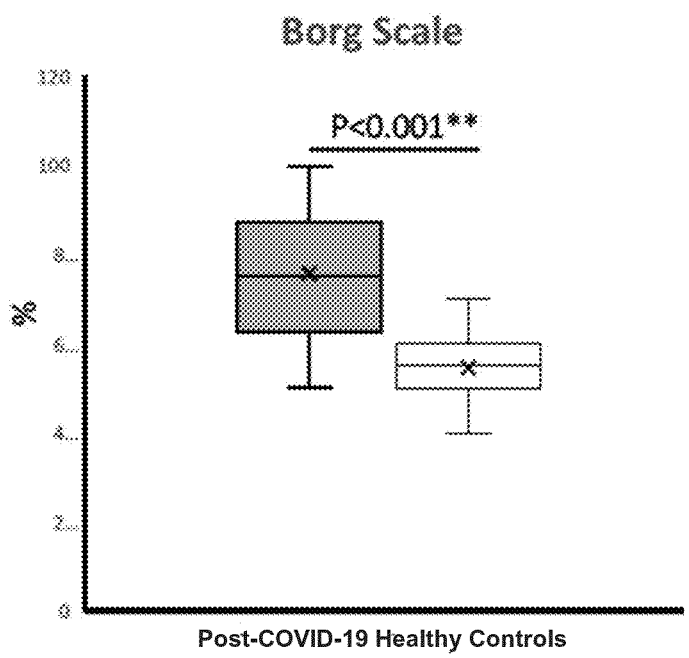
Figure 1C:
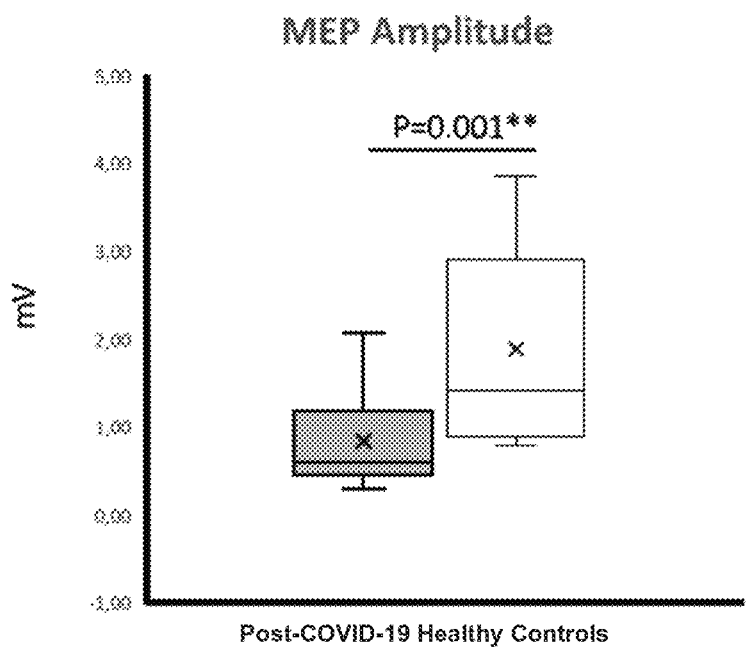
Figure 2:
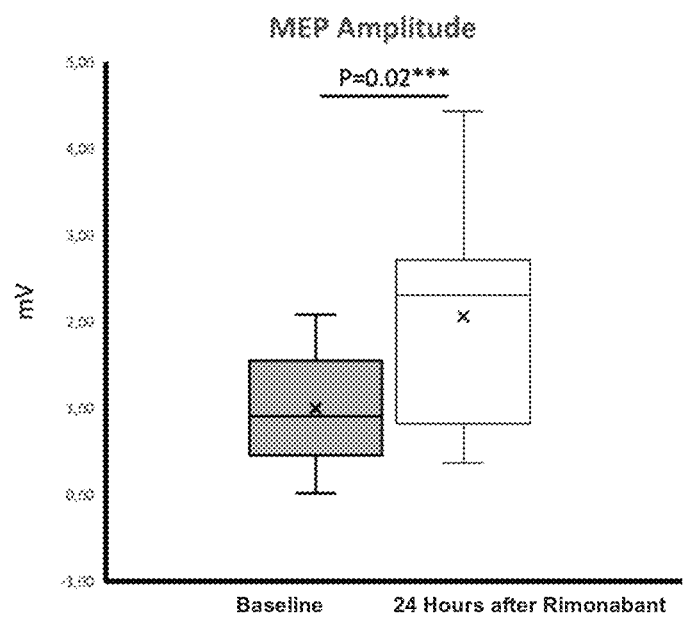
FIG. 2. In healthy subjects, motor system excitability was increased 24 hours after the administration of Rimonabant 20 mg (baseline: mean±S.D. 1.1±0.6 mV; 24 hours after rimonabant: mean±S.D. 2.1±1.2 mV; ***paired T test, p=0.02).

The following experiments were carried out using Rimonabant, but it is to be understood that in no way the scope of the present invention should be limited by the example below. To the contrary, what is proved for Rimonabant can be extended to other antagonists/inverse agonists of CB1 receptors.

Material and Methods

A large number of patients who recover from the acute phase of coronavirus disease 2019 (COVID-19), caused by the novel "severe acute respiratory syndrome coronavirus 2" (SARS-CoV-2), manifest a plethora of long-lasting symptoms. Among them, a high proportion of individuals (53.1%) experience fatigue. Fatigue may be related to disorders of the excitability of the motor system.

The aim of the present experiments was to use transcranial magnetic stimulation to test the motor system excitability in patients with COVID-19 related fatigue.

Neurophysiological examination was performed with a case control design and 12 COVID-19 patients were compared with 12 control age-matched individuals.

Using transcranial magnetic stimulation (TMS), we evaluated the MEP amplitude in the first dorsal interosseous muscle (FDI) at rest.

Subjects 12 healthy volunteers (mean age±S.D. 64.3±10.5 years) and 12 COVID 19 patients three months after the COVID-19 (mean age±S.D. 67.0±9.6 years) participated in all experiments. All the subjects gave their written informed consent.

Description of COVID-19 Group

General fatigue was measured using the fatigue severity score was higher in the COVID-19 group (median±S.D. 38±10.8) in comparison with healthy controls (median±S.D. 9.5±0.5, p<0.05).

Fatigue perception after a motor effort (1 min isometric task) was measured using the Borg Scale was higher in the COVID-19 group (median±S.D. 75±15.6) in comparison with healthy controls (median±S.D. 54.6±9.7, p<0.05).

Motor system excitability (MEP amplitude) was evaluated using transcranial magnetic stimulation in the COVID-19 group in comparison with healthy controls.

Magnetic stimulation was performed using a high-power Magstim 200 magnetic stimulator (Magstim Co., Whitland, UK). A figure-of-eight coil with external loop diameters of 9 cm was held over the right motor cortex at the optimum scalp position to elicit motor responses in the contralateral first dorsal interosseous (FDI). The induced current flowed in a postero-anterior direction. Resting motor threshold (RMT) was defined as the minimum stimulus intensity that produced a liminal motor evoked response (about 50 µV in 50% of 10 trials) at rest. The main variables we test are the RMT and MEP amplitude in the two groups. MEP amplitude was obtained at 120% RMT. MEP amplitudes were compared using unpaired t test. Motor system excitability was lower in the COVID-19 group (mean±S.D. 0.8±0.5 mV) in comparison with healthy controls (mean±S.D. 1.9±1.2 mV, p=0.008). To summarize, COVID-19 has lower MEP Amplitudes.

MEP amplitude reflects the excitability of the motor system (Brasil-Neto J P, Pascual-Leone A, Valls-Solé J, Cammarota A, Cohen L G, Hallett M. *Postexercise depression of motor evoked potentials: a measure of central nervous system fatigue*. Exp Brain Res 1993; 93(1): 181-4). Based on this consideration we demonstrated that the excitability of the human motor system is reduced in COVID-19.

Example 1. Effects of Rimonabant on the Excitability of Motor Cortex and of Spinal Motor Neurons As it is previously described, Rimonabant penetrates the blood-brain barrier and, at normally used doses (20 mg per day) to produce psychological effects in healthy humans with a broad range of symptoms.

The aim of the present experiments was to use transcranial magnetic stimulation to test the effects of a single dose of 20 mg of Rimonabant on the excitability of motor cortex and of spinal motor neurons.

Neurophysiological examination was performed before and 24 hours after the administration of a single dose of 20 mg of Rimonabant.

Using transcranial magnetic stimulation (TMS), it was evaluated the thresholds for electromyographic responses in the first dorsal interosseous muscle (FDI) at rest and during voluntary contraction.

Subjects

Nine healthy volunteers (mean age±S.D. 32.1±5.8 years) participated in all experiments. All the subjects gave their written informed consent.

Magnetic stimulation was performed using a high-power Magstim 200 magnetic stimulator (Magstim Co., Whitland, UK). A figure-of-eight coil with external loop diameters of 9 cm was held over the right motor cortex at the optimum scalp position to elicit motor responses in the contralateral first dorsal interosseous (FDI). The induced current flowed in a postero-anterior direction. Resting motor threshold (RMT) was defined as the minimum stimulus intensity that produced a liminal motor evoked response (about 50 µV in 50% of 10 trials) at rest. The main variables we test is the RMT and MEP amplitude before and 24 hours after the Rimonabant 20 mg. MEP amplitude was obtained at 120% RMT.

Rimonabant effects on vigilance were moderate and did not interfere with subjects' ability to fully comply with the requirements of the experimental protocol. Hitherto, three subjects experienced agitation and anxiety (this effect lasted an average of 6 hours) and one suffered for nausea (for 24 hours).

MEP amplitudes before and after Rimonabant were compared using paired t test. Administration of Rimonabant significantly increased the mean MEP amplitude (baseline: mean±S.D. 1.1±0.6 mV; 24 hours after rimonabant: mean±S.D. 2.1±1.2 mV; ***paired T test, p=0.02). These results show that Rimonabant increased MEP Amplitude, which reflects the excitability of the motor system (Brasil-Neto J P, Pascual-Leone A, Valls-Solé J, Cammarota A, Cohen L G, Hallett M. *Postexercise depression of motor evoked potentials: a measure of central nervous system fatigue*. Exp Brain Res 1993; 93(1): 181-4).

Based on this consideration it is demonstrated that the excitability of the human motor system is facilitated by CB1 antagonist Rimonabant.

Based on this consideration it is demonstrated that CB1 antagonist Rimonabant facilitates the excitability of the human motor system.

The invention claimed is:

1. A method of treating post-viral fatigue syndrome in COVID-19 patients, comprising administering a therapeutically effective amount of Rimonabant.

2. The method according to claim 1 wherein Rimonabant is administered in a form of administration selected from oral, sublingual, subcutaneous, intramuscular, intravenous, topical, local, intratracheal, intranasal, transdermal, and rectal.

3. A method of treating post-viral fatigue syndrome in COVID-19 patients comprising administering a therapeutically effective amount of a pharmaceutical composition comprising Rimonabant.

4. The method according to claim 3 wherein said pharmaceutical composition is administered in a form of administration selected from oral, sublingual, subcutaneous, intramuscular, intravenous, topical, local, intratracheal, intranasal, transdermal, and rectal.

5. The method according to claim 3 wherein said pharmaceutical composition contains an effective dose of Rimonabant, and at least one pharmaceutically acceptable excipient.

6. The method according to claim 5, wherein the effective daily dose of Rimonabant ranges from 1 mg to 50 mg per dose.

* * * * *